US011745157B2

(12) United States Patent
Shouche et al.

(10) Patent No.: US 11,745,157 B2
(45) Date of Patent: *Sep. 5, 2023

(54) OFF-GAS INCINERATOR CONTROL

(71) Applicant: INEOS EUROPE AG, Rolle (CH)

(72) Inventors: Manoj Shrikant Shouche, Pearland, TX (US); Timothy Robert McDonel, Elburn, IL (US); Jay Robert Couch, Naperville, IL (US)

(73) Assignee: INEOS EUROPE AG, Rolle (CH)

( * ) Notice: Subject to any disclaimer, the term of this patent is extended or adjusted under 35 U.S.C. 154(b) by 181 days.

This patent is subject to a terminal disclaimer.

(21) Appl. No.: 16/301,884

(22) PCT Filed: May 4, 2017

(86) PCT No.: PCT/US2017/030954
§ 371 (c)(1),
(2) Date: Nov. 15, 2018

(87) PCT Pub. No.: WO2017/205019
PCT Pub. Date: Nov. 30, 2017

(65) Prior Publication Data
US 2019/0282991 A1    Sep. 19, 2019

(30) Foreign Application Priority Data

May 24, 2016    (CN) .......................... 201610346931.6

(51) Int. Cl.
| | | |
|---|---|---|
| *C07C 253/26* | (2006.01) | |
| *C07C 255/08* | (2006.01) | |
| *B01J 19/00* | (2006.01) | |
| *C07C 253/28* | (2006.01) | |
| *C07C 253/24* | (2006.01) | |

(52) U.S. Cl.
CPC ......... *B01J 19/002* (2013.01); *B01J 19/0006* (2013.01); *B01J 19/0013* (2013.01); *C07C 253/24* (2013.01); *C07C 253/26* (2013.01); *C07C 253/28* (2013.01); *C07C 255/08* (2013.01); *B01J 2219/00051* (2013.01); *B01J 2219/00164* (2013.01); *B01J 2219/00216* (2013.01); *B01J 2219/00218* (2013.01); *B01J 2219/00243* (2013.01)

(58) Field of Classification Search
CPC .... C07C 253/26; C07C 255/05; C07C 255/08
See application file for complete search history.

(56) References Cited

U.S. PATENT DOCUMENTS

| | | | | |
|---|---|---|---|---|
| 3,544,616 A | * | 12/1970 | Friederich ................ | B01J 23/28 502/343 |
| 5,538,693 A | | 7/1996 | Olivier et al. | |
| 6,261,093 B1 | | 7/2001 | Matros et al. | |
| 11,078,156 B2 | * | 8/2021 | Shouche ................ | B01J 8/1809 |
| 2005/0187401 A1 | * | 8/2005 | Godbole .............. | C07C 253/34 558/463 |

FOREIGN PATENT DOCUMENTS

| | | | | |
|---|---|---|---|---|
| CN | 102452756 | | 5/2012 | |
| CN | 103212419 | | 7/2013 | |
| CN | 103864112 | | 6/2014 | |
| CN | 104421946 | | 3/2015 | |
| EP | 0381369 | | 8/1990 | |
| EP | 0381369 A1 | * | 8/1990 | |
| EP | 1188987 | | 3/2002 | |
| EP | 1188987 A2 | * | 3/2002 | ............. F23N 5/003 |
| GB | 2085318 | | 4/1982 | |
| JP | H10132241 | | 5/1998 | |
| JP | 2008080219 | | 4/2008 | |
| WO | 2009130180 | | 10/2009 | |

OTHER PUBLICATIONS

EPA, Acrylontrile Plant Air Pollution Control, Feb. 1979 (Year: 1979).*
Hughes et al., "Source Assessment: Acrylonitrile Manufacture (Air Emissions)," EPA-600/2-77-107j, Sep. 1977 (Year: 1977).*
Allen Houtz et al, Ratio Control and Metered-Air Combustion Processes—Control Guru, Internet article, retrieved from internet on Jul. 31, 2017, 10 pages.
A Tejeswar Reddy et al, Safety Enhancement of Furnace Using DCS by Feed Forward Control, International Journal of Advanced Research in Electrical Electronics and Instrumentation Engineering, Apr. 4, 2014, pp. 2320-3765.
National Intellectual Property Administration, PR China, Office Action issued in CN patent application 201610346931.6, dated Sep. 4, 2018, 12 pages.
International Searching Authority, Search Report and Written Opinion issued in PCT/US2017/030954, dated Oct. 12, 2017, 23 pages.

* cited by examiner

*Primary Examiner* — Matthew P Coughlin
(74) *Attorney, Agent, or Firm* — INEOS Europe AG

(57) ABSTRACT

A process provides for minimizing an amount of fuel gas utilized in an absorber off-gas incinerator and better control of emissions. The process provides for less temperature deviations in the absorber off-gas incinerator firebox and for less deviation in an amount of oxygen in the absorber off-gas incinerator stack gas.

6 Claims, 1 Drawing Sheet

OFF-GAS INCINERATOR CONTROL

A process is provided for controlling an off-gas incinerator. More specifically, the process includes minimizing an amount of fuel gas utilized in an absorber off-gas incinerator and controlling emissions from the incinerator.

BACKGROUND

Acrylonitrile is manufactured by an ammoxidation process where air, ammonia, and propylene are reacted in the presence of catalyst in a fluidized bed to form a vaporous reactor effluent. The vaporous reactor effluent is then passed to a quench system wherein the reactor effluent is directly contacted with an aqueous quenching liquid, usually water. This quenching removes unreacted ammonia and heavy polymers. The quenched gases then proceed to an absorption column. In the absorber, the gases are directly contacted with an absorbing liquid, again usually water. The water, acrylonitrile, acetonitrile, HCN and associated impurities leave the bottom of the absorber in an aqueous solution. Gases are removed from the top of the absorber. The gases removed from the top of the absorber are sent to an absorber off-gas incinerator (AOGI).

The absorber off-gas incinerator (AOGI) is used in the acrylonitrile process to burn the unabsorbed gas stream containing unreacted hydrocarbons, and a minor amount of acrylonitrile. The AOGI includes a heat recovery section that generates high-pressure steam used in other parts of the acrylonitrile process. In the AOGI, air and fuel gas are used to burn the absorber off-gas at a high temperature. The key variables to be controlled in the AOGI are the incinerator temperature and the stack O2. Tighter control of these two variables is desired from an emission control point of view. This control objective is desired not only during normal operations, but also during rate changes and also when the propylene purity changes.

Model Predictive Control (MPC), also known as Advanced Process Control (APC), uses a process model to predict the behavior of a process into the future and then implements an optimized control action to counter process deviation from a desired target. Along with controlling the process, MPC also tries to drive the process towards the most "economic" condition by moving the key process variables.

SUMMARY

A process provides for minimizing an amount of fuel gas utilized in an absorber off-gas incinerator and better control of emissions. The process provides for less temperature deviations in the absorber off-gas incinerator firebox and for less deviation in an amount of oxygen in the absorber off-gas incinerator stack gas. Reducing standard deviations in absorber off-gas incinerator firebox temperature and absorber off-gas incinerator stack oxygen provides a reduction in fuel gas usage and tighter control of environmental variables. These control objectives are achieved during normal operations, during rate changes, and when propylene purity changes. Unexpectedly, the process provides control of AOGI temperature and O2 in AOGI stack gas by determining an amount of hydrocarbon in the reactor feed stream and the feed rate of the reactor feed stream.

The process includes measuring an ammoxidation reactor feed rate and a purity of hydrocarbon feed into the reactor. In accordance with the process, the reactor feed rate and hydrocarbon purity effect an amount of fuel gas flow and air flow to the off-gas incinerator. In an important aspect, an operator can predict off-gas incinerator performance based on a known reactor feed rate and hydrocarbon purity and then implement controls to minimize AOGI temperature and oxygen deviations in the off-gas incinerator stack gas.

A process for operating an off-gas incinerator includes introducing a flow of a reactant stream into an ammoxidation reactor; determining an amount of hydrocarbon in the reactant stream and determining a feed rate of the reactant stream; conveying a reactor effluent from the ammoxidation reactor to an absorber; supplying an absorber off-gas from the absorber to an absorber off-gas incinerator; and supplying fuel gas and air to the absorber off-gas incinerator. The absorber off-gas, fuel gas, and air are supplied to the absorber off-gas incinerator in amounts to maintain about 6 kg or less $NO_x$ in an absorber off-gas incinerator stack gas per ton AN produced in the plant and about 3.5 kg or less non-methane hydrocarbon in absorber off-gas incinerator stack gas per ton AN produced in the plant.

A process for operating an off-gas incinerator includes introducing a flow of a reactant stream into an ammoxidation reactor; determining an amount of hydrocarbon in the reactant stream and determining a feed rate of the reactant stream; conveying a reactor effluent from the ammoxidation reactor to an absorber; supplying an absorber off-gas from the absorber to an absorber off-gas incinerator; and supplying fuel gas and air to the absorber off-gas incinerator. In one aspect, the absorber off-gas, fuel gas, and air are supplied to the absorber off-gas incinerator in amounts to maintain a temperature in the off-gas incinerator within about 10° F. of a temperature set point of the off-gas incinerator.

In another aspect, a process for operating an off-gas incinerator includes introducing a flow of a reactant stream into an ammoxidation reactor; determining an amount of hydrocarbon in the reactant stream and determining a feed rate of the reactant stream; conveying a reactor effluent from the ammoxidation reactor to an absorber; supplying an absorber off-gas from the absorber to an absorber off-gas incinerator; and supplying fuel gas and air to the absorber off-gas incinerator. In one aspect, a set of manipulated variable includes fuel gas flow to the absorber off-gas incinerator and the air flow to the absorber off-gas incinerator, and a set of controlled variables includes an amount of oxygen in the absorber off-gas incinerator stack and a temperature in the absorber off-gas incinerator. The process includes controlling at least one set of controlled variables by adjusting manipulated variables. In this aspect, manipulated variables are changed based on feedforward variables.

BRIEF DESCRIPTION OF FIGURES

The above and other aspects, features and advantages of several aspects of the process will be more apparent from the following figures.

Figure 1:
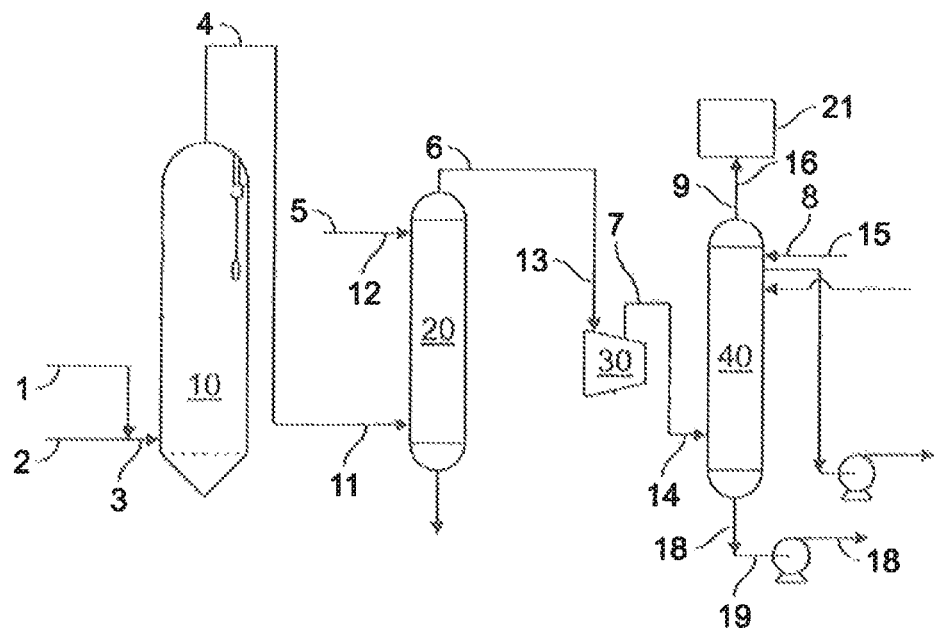
FIG. 1 illustrates an ammoxidation process.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various aspects. Also, common but well-understood elements that are useful or necessary in a commercially feasible aspect are often not depicted in order to facilitate a less obstructed view of these various aspects.

DETAILED DESCRIPTION

The following description is not to be taken in a limiting sense, but is made merely for the purpose of describing the general principles of exemplary embodiments. The scope of the invention should be determined with reference to the claims.

The Ammoxidation Process

FIG. 1 is a schematic flow diagram of an ammoxidation process. Referring to the figure, the process includes a reactor 10, quench vessel 20, an optional effluent compressor 30, and absorber 40. Ammonia in stream 1 and hydrocarbon (HC) feed in stream 2 may be fed as combined stream 3 to reactor 10. HC feed stream 2 may include a hydrocarbon selected from the group consisting of propane, propylene, isobutene, isobutylene, and combinations thereof. In one aspect, the hydrocarbon is mainly propylene. A catalyst (not shown in FIG. 1) may be present in reactor 10. Oxygen containing gas may be fed to reactor 10. For example, air may be compressed by an air compressor (not shown in FIG. 1) and fed to reactor 10.

Acrylonitrile is produced in reactor 10 from the reaction of the hydrocarbon, ammonia, and oxygen in the presence of a catalyst in reactor 10. The stream that includes acrylonitrile may exit out of a top portion of reactor 10 as reactor effluent stream 4. Reactor effluent stream 4 that includes acrylonitrile produced in reactor 10 may be conveyed through line 11 to quench vessel 20.

In quench vessel 20, reactor effluent stream 4 may be cooled by contact with quench aqueous stream 5 entering quench vessel 20 via line 12. Quench aqueous stream 5 may include an acid in addition to water. The cooled reactor effluent that includes acrylonitrile (including co-products such as acetonitrile, hydrogen cyanide and impurities) may then be conveyed as quenched stream 6 to effluent compressor 30 via line 13.

Quenched stream 6 may be compressed by effluent compressor 30, and exit effluent compressor 30 as compressor effluent stream 7. The process may include operating without the compressor. Compressor effluent stream 7 may be conveyed to a lower portion of absorber 40 via line 14. In absorber 40, acrylonitrile may be absorbed in a second or absorber aqueous stream 8 that enters an upper portion of absorber 40 via line 15. The aqueous stream or rich water stream 18 that include acrylonitrile and other co-products may then be transported from absorber 40 via line 19 a recovery column (not shown in FIG. 1) for further product purification. The non-absorbed effluent 9 exits from the top of absorber column 40 through pipe 16. Non-absorbed effluent or absorber effluent 9 may include off-gases, which can be burned in absorber off-gas incinerator 21 (AOGI) or absorber off-gas oxidizer (AOGO).

Operation of AOGI

Figure 2:
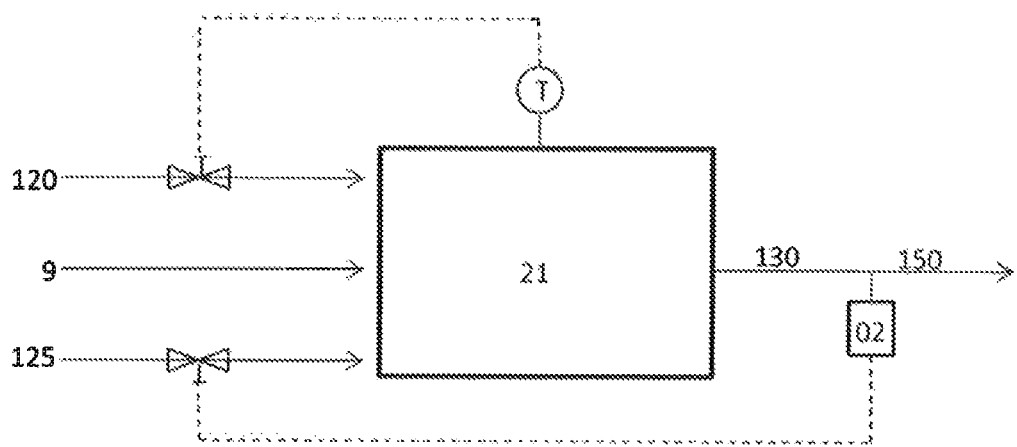
FIG. 2 shows a more detailed view of an AOGI.

A more detail view of the AOGI 21 is shown in FIG. 2. As shown in FIG. 2, absorber effluent 9, fuel gas 120, and air 125 enter an AOGI 21. AOGI effluent gas 130 is sent to an AOGI stack 150.

Environmental permit requirements may define operating parameters for the AOGI. For example, environmental requirement may require operations to provide less than required amounts of NOx, non-methane hydrocarbon, and/or CO in the AOGI stack gas. Monitoring of amounts of each of these compounds in AOGI stack gas is by methods known in the art. The process may include a continuous emission monitoring system (CEMS). The environmental requirements do not directly control AOGI operation but help to define operating conditions and set points needed to attain environmental requirements.

In one aspect, the process includes operating the AOGI to control $NO_x$ levels in the AOGI stack gas. In this aspect, the process includes providing absorber effluent, fuel gas and air to the AOGI in amounts to maintain about 6 kg or less $NO_x$ per ton AN produced in the plant, in another aspect, about 5 kg or less $NO_x$, in another aspect, about 4 kg or less NOx, and in another aspect, about 3 kg or less $NO_x$ per ton AN produced in the plant. In this aspect, the process includes measuring $NO_x$ in the AOGI stack gas.

In another aspect, the process includes operating the AOGI to control non-methane hydrocarbon (NMHC) in the AOGI stack gas. In this aspect, NMHC mainly includes propane, acrylonitrile, acetonitrile, and propylene. In this aspect, the process includes providing absorber effluent, fuel gas and air to the AOGI in amounts to maintain about 3.5 kg or less NMHC per ton AN produced in the plant, in another aspect, about 3 kg or less NMHC, in another aspect, about 2.5 kg or less NMHC, and in another aspect, about 2 kg or less NMHC per ton AN produced in the plant. In this aspect, the process includes measuring NMHC in the AOGI stack gas.

In another aspect, the process includes operating the AOGI to control CO in the AOGI stack gas. In this aspect, the process includes providing absorber effluent, fuel gas and air to the AOGI in amounts to maintain about 3.5 kg or less CO per ton AN produced in the plant, in another aspect, about 3 kg or less CO, in another aspect, about 2.5 kg or less CO, and in another aspect, about 2.0 kg or less CO per ton AN produced in the plant. In this aspect, the process includes measuring CO in the AOGI stack gas.

In one aspect, the process includes supplying an absorber effluent from the absorber to the AOGI 21 and supplying fuel gas 120 and air 125 to the AOGI 21. The absorber effluent, fuel gas and air are supplied to the AOGI in amounts to maintain a temperature in the AOGI within about 10° F. of a temperature set point of the AOGI by varying a fuel gas supply rate, and in another aspect, within about 5° F. of a temperature set point of the AOGI. In this aspect, temperature is measured inside the AOGI 21. The process may include various known configurations for heat exchangers. In one aspect, the absorber off-gas incinerator temperature set point is the minimum temperature necessary to achieve less than the required amounts of $NO_x$, non-methane hydrocarbon, and/or CO in the absorber off-gas incinerator stack gas, preferably minimum temperature necessary to achieve less that than the required amounts of each of them.

In one aspect, the absorber off-gas includes unreacted propylene. The reactor includes control and shutdown systems to make sure explosive levels of propylene do not go to the AOGI. In this aspect, reactor temperature control and shutdown systems will detect loss of reaction and prevent excess propylene flow to the AOGI.

In another aspect, the process includes controlling an amount of oxygen in the absorber off-gas incinerator stack gas in part, by varying air 125 supplied to the AOGI. In this aspect, the amount of oxygen in the absorber off-gas incinerator stack gas is about 5 volume % or less, in another aspect, about 3.5 volume % or less, in another aspect, about 3 volume % or less, in another aspect, about 2.5 volume % or less, in another aspect, about 2 volume % or less, and in another aspect, at least about 1 volume % or less. Oxygen is measured in the AOGI stack 150.

In another aspect, the process provides for an overall process acrylonitrile recovery of about 95 to about 97%. The associated quench and absorber efficiencies are greater than about 99%. In this aspect, a ratio of fuel gas supplied to the absorber off-gas incinerator to acrylonitrile produced is maintained in a range of about 3.3:1 thousand standard cubic feet per ton acrylonitrile (MSCF/T) to about 3.8:1 (MSCF/T), and in another aspect, about 3.4:1 (MSCF/T) to about 3.7:1 (MSCF/T). In a related aspect, a ratio of air supplied to the absorber off-gas incinerator to acrylonitrile produced is maintained in a range of about 1.7:1 thousand standard cubic feet per minute per ton of acrylonitrile (MSCFM/T/hr AN) to about 1.9:1 (MSCFM/T/hr AN).

The fluidized bed reactor is at the heart of an acrylonitrile plant. It is desirable to ensure that reactor efficiency (including in terms of reagent conversion and catalyst losses) is optimized whilst increasing the specific capacity of the reactor. Failure to correctly operate a reactor could at significantly affect the efficiency, reliability or production capacity of an entire acrylonitrile plant and in the extreme lead to an extended shut-down of production. The operation and performance of a fluidized bed is highly sensitive to the specific operating conditions selected and the industry is highly cautious in changing such conditions. As the fluidized bed operating conditions change (eg. reactor pressure, reactor gas velocity, bed height, ratio of bed pressure drop to grid pressure drop etc) and catalyst characteristics change (particle size, particle size distribution, fines content, attrition characteristics), so too can the catalyst performance and associated production capability and efficiency. An ammoxidation process includes reacting ammonia, oxygen, and a hydrocarbon selected from the group consisting of propane, propylene, isobutane and isobutylene, and combinations thereof in the presence of a catalyst, at a pressure (absolute) of about 140 kPa or less and a velocity of about 0.5 to about 1.2 meters/second to provide a reactor effluent stream. When using a catalyst with an average particle diameter between about 10 and 100μ, with a particle size distribution where about 0 to 30 weight percent is greater than about 90μ, and about 30 to 50 weight percent is less than 45μ, the fluidization velocity (based on effluent volumetric flow and reactor cross-sectional area ("CSA") excluding cooling coils and dip legs area) can be operated at up to 1.2 m/s, preferably between 0.55 and 0.85. Even at up to the indicated velocities it has been found possible to operate with acceptable catalyst loses while operating the reactor with a top pressure of about 0.50 to about 0.58 kg/cm$^2$ and/or cyclones with a pressure drop of 15 kPa or less, and a fines disengagement height above the top of the fluidized bed of about 5.5 to about 7.5 m. This leads to potential for increased production capacity per unit reactor volume (tangent to tangent) of between 0.005 and 0.015 metric tons per hour per cubic meter of reactor volume, in another aspect, about 0.0075 to about 0.0125, and in another aspect, about 0.009 to about 0.01 metric tons per hour per cubic meter of reactor volume.

In an aspect, the process includes operating or reacting in a reactor a hydrocarbon, wherein the effluent volumetric flow has a velocity of about 0.5 to about 1.05 m/sec (based on effluent volumetric flow and reactor cross-sectional area ("CSA") excluding cooling coils and dip legs area, i.e., ~90% of open CSA). It has been found that it is possible to design and operate the reactor system using this velocity whilst also achieving good fluidization/catalyst performance and reasonable catalyst entrainment/catalyst losses from cyclones, such that velocities may be maintained in about this range to the extent possible as reactor capacity is increased. In an embodiment, the reactor may be operated with a velocity of up to about 0.75 msec to about 0.95 msec (based on 90% CSA and effluent gas), and maintain a top pressure of about 0.50 to about 0.65 kg/cm$^2$, and in another aspect, about 0.52 to about 0.58 kg/cm$^2$. In one aspect, a ratio of cyclone inlet velocity in meters/second to a reactor effluent velocity in meters/second is about 15 or greater, in another aspect, about 20 or greater, in another aspect, about 15 to about 30, in another aspect, about 20 to about 30, in another aspect, about 22 to about 25, in another aspect, about 23 to about 26, and in another aspect, about 27 to about 29.

In an aspect, the process includes operating or reacting in a reactor a hydrocarbon, wherein the reactor has a fluidized bed height that is about 25% to about 60% of the reactor cylindrical height (tangent to tangent), in another aspect, about 25% to about 37%, in another aspect, about 42% to about 50%, in another aspect, about 45% to about 55%, and in another aspect, about 44% to about 47%.

In an aspect, the process includes operating or reacting in a reactor a hydrocarbon, wherein the reactor has a fluidized bed height that is about 60% to about 110% of the reactor diameter, in another aspect, about 60% to about 80%, in another aspect, about 70% to about 100%, in another aspect, about 75% to about 90%, in another aspect, about 80% to about 90%, in another aspect, about 85% to about 95%, in another aspect, about 70% to about 85%, and in another aspect, about 85% to about 90%.

In an aspect, the process includes operating or reacting in a reactor a hydrocarbon, wherein the reactor has a top pressure in the range of about 0.50 to about 0.65 kg/cm$^2$, in another aspect, about 0.52 to about 0.58 kg/cm$^2$, in another aspect, about 0.54 to about 0.6 kg/cm$^2$, and in another aspect, about 0.5 to about 0.55 kg/cm$^2$. A reactor top pressure in this range provides the benefit of improved catalyst performance over a reactor top pressure that is higher than this range. In an aspect, the method includes operating the reactor in the range of about 0.54 to about 0.56 kg/cm$^2$.

In an aspect, the process includes operating or reacting in a reactor a hydrocarbon, wherein the amount of ammonia in the reactor feed to provide an ammonia to hydrocarbon molar ratio of about 1 to about 2, in another aspect, about 1.25 to about 1.75, in another aspect, about 1.4 to about 1.6, and in another aspect, about 1.25 to about 1.3.

In another aspect, a process includes operating or reacting in a reactor a hydrocarbon, wherein the an amount of air in the reactor feed provides an air to hydrocarbon ratio of about 9 to about 12 in the reactor feed, in another aspect, a ratio of about 9 to about 11, in another aspect, a ratio of about 9 to about 10, in another aspect, a ratio of about 10.5 to about 11, in another aspect, a ratio of about 9.25 to about 9.75, and in another aspect, a ratio of about 9.4 to about 9.6. In a related aspect, the reactor effluent stream includes about 0.5 to about 1 weight % oxygen. The process may further include continuously measuring the amount of oxygen in the reactor effluent and continuously adjusting the molar ratio of air to hydrocarbon in response. Oxygen may be measured at any location downstream of the reactor.

A process for absorbing a reactor effluent stream that includes acrylonitrile, includes quenching the reactor effluent stream with a first aqueous stream to provide a quenched stream that includes acrylonitrile; compressing the quenched stream to provide an effluent compressor stream that includes acrylonitrile; conveying the effluent compressor stream to an absorber at a pressure (absolute) of about 300 kPa to about 500 kPa; and in the absorber, absorbing acrylonitrile in a second aqueous stream to provide a rich water that includes acrylonitrile.

In another aspect, a process for absorbing a reactor effluent stream that includes acrylonitrile, the process includes quenching the reactor effluent stream with a first aqueous stream to provide a quenched stream that includes acrylonitrile; compressing the quenched stream to provide an effluent compressor stream that includes acrylonitrile; conveying the effluent compressor stream to an absorber; and in the absorber, absorbing acrylonitrile in a second aqueous stream having a temperature of about 4° C. to about 45° C. to provide a rich water that includes acrylonitrile.

Changes in reactor, quench and/or absorber operation can effect AOGI operating parameters needed to attain desired emission levels. For example, changes in reactor conversion rates and may effect the absorber off-gas composition and effect how much fuel and oxygen need to be supplied to the AOGI. In this aspect, reactor propylene conversion rates will be about 95% to less than about 100%. As used herein, "reactor propylene conversion rates" refers to a percentage of an amount of propylene in the reactor feed that is converted to acrylonitrile and other carbon containing products. In another aspect, quench column operation may effect absorber column temperature which may ultimately effect how much water is in the absorber off-gas. Changes in water content of the absorber off-gas may then impact AOGI operation. In this aspect, quench column effluent having a temperature of about 65° C. to about 85° C. (for one type of quench design) and about 100° C. to about 120° C. (for another type of quench design) is conveyed to the absorber. In a related aspect, absorber off-gas has about 5 weight % or less water and the level of water in the absorber off-gas may vary as the temperature at the top of the absorber varies. In another aspect, the quench column may provide a pH of about 3.5 to about 7, in another aspect, about 3.5 to about 6, and in another aspect, about 5 to about 5.5 in the condensate from the quench column aftercooler.

Advanced Process Control

Changes in reactor feed rate (hydrocarbon feed rate) changes the amount of propane coming into the absorber and eventually into the AOGI. Propane has been found to be essentially inert in the reactor with catalyst. Propane acts as a fuel and can cause AOGI temperature and stack O2 deviation if the change is not countered with fuel gas flow in a feedforward manner. The same can be seen in the case when the propylene purity changes, which results in different amount of propane coming to the absorber and AOGI. Thus, knowing the feed rate and propylene purity (and the changes in those) can provide better control of the AOGI firebox temperature and stack O2 when the changes are used to predict the deviation in AOGI temperature and O2, and then countered with a fuel gas change.

A model predictive control (MPC), also known as advanced process control (APC), uses a process model to predict the behavior of a process into the future, and then implements an optimized control action to counter process deviation from a desired target. Along with controlling the process, MPC also tries to drive the process towards the most "economic" condition by moving the key process variables. The process includes using MPC to achieve reduced fuel gas usage and improved AOGI emissions.

As used herein, the term "manipulated variable" refers to variables that are adjusted by the advanced process controller. In this aspect manipulated variables include fuel gas flow rate and air flow rate to the AOGI. The term "controlled variables" refers to variables that are kept by the advanced process controller at a predetermined value (set point) or within a predetermined range (set range). In this aspect, controlled variable include temperature in the AOGI and $O_2$ in the AOGI stack gas. "Optimizing a variable" refers to maximizing or minimizing the variable and to maintaining the variable at a predetermined value. "Feedforward variable" refers to variables used in determining adjustments to the manipulated variables. In this aspect, feedforward variables include flow rate of a reactant stream into an ammoxidation reactor and an amount of hydrocarbon in the reactant stream.

One aspect of model predictive control is that future process behavior is predicted using a model and available measurements of the controlled variables. The controller outputs are calculated so as to optimize a performance index, which is a linear or quadratic function of the predicted errors and calculated future control moves. At each sampling instant, the control calculations are repeated and predictions updated based on current measurements. In this aspect, a suitable model is one that includes a set of empirical step-response models expressing the effects of a step-response of manipulated variables and feedforward variables on the controlled variables.

An optimum value for the parameter to be optimized can be obtained from a separate optimization step, or the variable to be optimized can be included in the performance function.

Before model predictive control can be applied, one determines first the effect of step changes of the manipulated variables on the variable to be optimized and on the controlled variables. This results in a set of step-response coefficients. This set of step-response coefficients forms the basis of the model predictive control of the process.

During normal operation, the predicted values of the controlled variables are regularly calculated for a number of future control moves. For these future control moves a performance index is calculated. The performance index includes two terms, a first term representing the sum over the future control moves of the predicted error for each control move and a second term representing the sum over the future control moves of the change in the manipulated variables for each control move. For each controlled variable, the predicted error is the difference between the predicted value of the controlled variable and a reference value of the controlled variable. The predicted errors are multiplied with a weighting factor, and the changes in the manipulated variables for a control move are multiplied with a move suppression factor.

Alternatively, the terms may be a sum of squared terms, in which case the performance index is quadratic. Moreover, constraints can be set on manipulated variables, change in manipulated variables and on controlled variables. This results in a separate set of equations that are solved simultaneously with the minimization of the performance index.

Optimization can be done in two ways; one way is to optimize separately, outside the minimization of the performance index, and the second way is to optimize within the performance index.

When optimization is done separately, the variables to be optimized are included as controlled variables in the predicted error for each control move and the optimization gives a reference value for the controlled variables.

Alternatively, optimization is done within the calculation of the performance index, and this gives a third term in the performance index with an appropriate weighting factor. In this case, the reference values of the controlled variables are pre-determined steady state values, which remain constant.

The performance index is minimized taking into account the constraints to give the values of the manipulated variables for the future control moves. However, only the next control move is executed. Then the calculation of the performance index for future control moves starts again.

The models with the step response coefficients and the equations required in model predictive control are part of a computer program that is executed in order to control the absorber off-gas incineration process. A computer program loaded with such a program that can handle model predictive control is called an advanced process controller. Commercially available computer programs that may be utilized include for example, DMCplus® by Aspen Technology and PredictPro® by Emerson.

EXAMPLES

Example 1: Fuel Gas and Air Usage at 16 T/hr Acrylonitrile

Effect of AOGI Temperature Changes: The following Table compares fuel gas and air usage when operating a plant to produce 16 T/hr acrylonitrile (AN). A baseline operation describes optimal AOGI temperature and stack O2. In practice, the process may include operating the AOGI at about 10° F. higher to provide a buffer for changes in feed purity and reactor feed rates. As shown in the Table, when temperature is raised 10° F. and stack O2 is held constant, fuel gas usage air usage increases. In this example, fuel gas usage in the +10° operation increased about 6.9% and air usage increased about 2.1% as compared to the baseline operation. In this aspect, fuel gas usage may increase about 6% to about 7.5% and air usage may increase about 1.5% to about 2.5% as compared to operating the AOGI at a temperature of about 10° F. over a baseline operation.

Effect of AOGI Temperature Changes and Stack O2 Changes: As further shown in the Table, when stack O2 increases from 1.4% to 1.6%, fuel gas usage increased about 15% and air usage increased about 7.4% as compared to the baseline operations. In this aspect, fuel gas usage may increase from about 12% to about 16% and air usage may increase about 6% to about 8% as compared to operating the AOGI at a stack O2 of about 1.4% and a baseline temperature. The process provided herein reduces the need to operate the AOGI at +10° F. above a desired baseline and results in savings in fuel gas and air provided to the AOGI.

Effect of Feedstock Purity Changes: The following Table illustrates the effect of feedstock purity changes. As shown in the Table, when feedstock purity decreases 1% and fuel gas and air are maintained at baseline levels, the AOGI temperature increases. Where a baseline temperature is maintained, fuel gas usage declines and air remains the same.

The process provided herein allows for a proactive adjustment of fuel gas feed to the AOGI based purity changes in the feedstock. This proactive adjustment of fuel gas feed allows the AOGI to stay closer to its desired temperature while using less fuel gas. In this aspect, fuel gas usage at a feedstock purity of about 95.4% was about 49.1% less than a baseline operation when fuel gas was allowed to decrease to maintain AOGI temperature.

| 16.4 T/hr AN | | | | |
|---|---|---|---|---|
| | AOGI Temp ° F. | C3 % | Stack O2 % | Fuel Gas MSCF/T AN | Air MSCFM/T/hr AN |
| Baseline | 1470 | 96.4 | 1.4 | 1.16 | 0.95 |
| +10° | 1480 | 96.4 | 1.4 | 1.24 | 0.97 |
| +10° > O2 | 1480 | 96.4 | 1.6 | 1.31 | 1.02 |
| Baseline FG and Air | 1566 | 95.4 | — | 1.16 | 0.95 |
| Baseline temperature | 1470 | 95.4 | — | 0.57 | 0.95 |

Example 2: Fuel Gas and Air Usage at 12 T/Hr Acrylonitrile

Effect of AOGI Temperature Changes: The following Table compares fuel gas and air usage when operating a plant to produce 12 T/hr acrylonitrile (AN). A baseline operation describes optimal AOGI temperature and stack O2. In practice, the process may include operating the AOGI at about 10° F. higher to provide a buffer for changes in feed purity and reactor feed rates. As shown in the Table, when temperature is raised 10° F. and stack O2 is held constant, fuel gas usage increases. In this example, fuel gas usage in the +10° operation increased about 3.7% and air usage increased about 0.8% as compared to the baseline operation. In this aspect, fuel gas usage may increase about 3% to about 4% and air usage may increase about 0.5% to about 1.0% as compared to operating the AOGI at a temperature of about 10° F. over a baseline operation.

Effect of AOGI Temperature Changes and Stack O2 Changes: As further shown in the Table, when stack O2 increases from 2.6% to 2.8%, fuel gas usage increased about 7.7% and air usage increased about 6.0% as compared to the baseline operations. In this aspect, fuel gas usage may increase from about 5% to about 10% and air usage may increase about 5% to about 7% as compared to operating the AOGI at a stack O2 of about 2.6% and a baseline temperature.

Effect of Feedstock Purity Changes: The following Table illustrates the effect of feedstock purity changes. As shown in the Table, when feedstock purity decreases 1% and fuel gas and air are maintained at baseline levels, the AOGI temperature increased 5.8% over the baseline temperature. In this aspect, a decrease in feedstock purity may result in an increase in AOGI temperature of about 5.5% to about 6.5% over the baseline temperature. When feedstock purity increases 1% and fuel gas and air are maintained at baseline levels, the AOGI temperature decreases about 6.2% over the baseline temperature. In this aspect, an increase in feedstock purity may result in a decrease in AOGI temperature of about 5.5% to about 6.5%.

| 12 T/hr AN | | | | |
|---|---|---|---|---|
| | AOGI Temp ° F. | C3 % | Stack O2 % | Fuel Gas MSCF/T AN | Air MSCFM/T/hr AN |
| Baseline | 1472 | 96.4 | 2.6 | 2.33 | 1.33 |
| +10° | 1482 | 96.4 | 2.6 | 2.42 | 1.34 |
| +10° > O2 | 1482 | 96.4 | 2.8 | 2.51 | 1.41 |
| Baseline FG and air | 1558 | 95.4 | 2.1 | 2.33 | 1.33 |
| Baseline FG and air | 1380 | 97.4 | 3.1 | 2.33 | 1.33 |

Example 3: Effect of Feedstock Purity and Feed Rates

Effect of Feedstock Purity Changes: The following Table illustrates the effect of feedstock purity changes. As shown in the Table, when feedstock purity increases 1.1% and fuel gas and air are maintained at baseline levels, the AOGI temperature decreased about 4.5%. In this aspect, an increase in feedstock purity of about 1.1% may result in a decrease in AOGI temperature of about 4% to about 5%.

When feedstock purity increases 1.1% and AOGI temperature is maintained at baseline levels, the fuel gas usage increased 16.5% and air usage increased 0.7%. In this aspect, when feedstock purity increases 1.1% and the AOGI temperature is maintained at baseline levels, fuel gas usage may increase from about 16% to about 17% over baseline levels, and air usage may increase from about 0.5% to about 1% over baseline levels.

|  | AOGI Temp ° F. | C3 % | Stack O2 % | Fuel Gas MSCF/T AN | Air MSCFM/T/hr AN |
|---|---|---|---|---|---|
| Baseline | 1614 | 92.9 | 1.42 | 3.21 | 1.47 |
| Baseline FG and air | 1542 | 94 | 1.83 | 3.21 | 1.47 |
| Baseline temperature | 1614 | 94 | 1.42 | 3.74 | 1.48 |

Effect of Reactor Feed Rates: The following Table illustrates the effect of changes in reactor feed rates. As shown in the Table, when the feed rate is increased 5% and fuel gas and AOGI temperature is maintained at baseline levels, the AOGI temperature decreased about 2° F. and stack O2 decreased about 13.4%. When the feed rate is decreased 10% and fuel gas and AOGI temperature is maintained at baseline levels, the AOGI temperature increased about 6° F. and stack O2 increased about 31%. When feed rate is decreased 10% and the AOGI temperature and stack O2 are maintained at baseline levels, the fuel gas usage decreased by about 10% and the air usage decrease by about 10.2%. In this aspect, a feed rate decrease of about 10% may result in a decrease in fuel usage of about 8% to about 12% and an air usage decrease of about 9.5% to about 10.5%.

|  | Rx Feed % Δ | AOGI Temp ° F. | Stack O2 % | Fuel Gas MSCF/T AN | Air MSCFM/T/hr AN |
|---|---|---|---|---|---|
| Baseline | — | 1614 | 1.42 | 3.21 | 1.47 |
| Baseline FG and air | +5 | 1612 | 1.23 | 3.21 | 1.47 |
| Baseline FG and air | −10 | 1620 | 1.86 | 3.21 | 1.47 |
| Baseline temperature | −10 | 1614 | 1.42 | 2.89 | 1.32 |

While the invention herein disclosed has been described by means of specific embodiments, examples and applications thereof, numerous modifications and variations could be made thereto by those skilled in the art without departing from the scope of the invention set forth in the claims.

What is claimed is:

1. A process for operating an off-gas incinerator, the process comprising:
    introducing a flow of reactant stream into an ammoxidation reactor, wherein the reactant stream includes ammonia, an oxygen containing gas, and a hydrocarbon selected from the group consisting of propane, propylene, or mixtures thereof;
    determining amount of hydrocarbon in the reactant stream being introduced into the ammoxidation reactor and determining a feed rate of the reactant stream to the ammoxidation reactor, wherein a hydrocarbon conversion rate is about 95% to less than 100%;
    conveying a gaseous reactor effluent from the ammoxidation to a quench vessel to provide a quenched stream;
    conveying the quenched stream to an absorber wherein acrylonitrile is absorbed from the quenched stream with an aqueous solution;
    supplying an absorber off-gas from the absorber to an absorber off-gas incinerator, wherein the absorber off-gas has about 5 weight % or less water;
    supplying fuel gas and air to the absorber off-gas incinerator; and
    using the amount of hydrocarbon in the reactant stream being introduced into the ammoxidation reactor and the feed rate of the reactant stream to the ammoxidation reactor in a model predictive control system to adjust the fuel gas flow to the absorber off-gas incinerator and the air flow to the absorber off-gas incinerator in an amount effective for maintaining a temperature in the absorber off-gas incinerator within about 10° F. of a temperature set point of the off-gas incinerator and for providing about 5 volume % or less oxygen in the absorber off-gas incinerator,
    wherein the process maintains about 6 kg or less NOx in the absorber incinerator off-gas per ton of acrylonitrile produced.

2. The process of claim 1 wherein the process includes controlling the amount of oxygen in the absorber off-gas incinerator and the temperature in the absorber off-gas incinerator based on model predictive control,
    wherein the model predictive control determines an effect of changes in the amount of hydrocarbon in the reactor stream and the feed rate of the reactant stream on off-gas incinerator temperature and oxygen and adjusts the fuel gas flow and air flow to the off-gas incinerator.

3. The process of claim 1 wherein the temperature in the absorber off-gas incinerator is maintained within about 5° F. of the temperature set point of the absorber off-gas incinerator.

4. The process of claim 1 wherein the hydrocarbon is propylene.

5. The process of claim 1 wherein the quenched stream conveyed to the absorber has a temperature of about 65° C. to about 85° C.

6. The process of claim 1 wherein the quenched stream conveyed to the absorber has a temperature of about 100° C. to about 120° C.

* * * * *